US00PP24378P3

(12) United States Plant Patent
Bak et al.

(10) Patent No.: US PP24,378 P3
(45) Date of Patent: Apr. 8, 2014

(54) ***VRIESEA* PLANT NAMED 'GLORY'**

(50) Latin Name: ***Vriesea* sp.**
Varietal Denomination: Glory

(75) Inventors: Elly Bak, Rijsenhout (NL); Nicolaas D. M. Steur, Oude Niedorp (NL)

(73) Assignee: Corn.Bak B.V., Assendelft (NL)

( * ) Notice: Subject to any disclaimer, the term of this patent is extended or adjusted under 35 U.S.C. 154(b) by 58 days.

(21) Appl. No.: 13/507,209

(22) Filed: Jun. 13, 2012

(65) Prior Publication Data

US 2013/0340137 P1 Dec. 19, 2013

(51) Int. Cl.
*A01H 5/00* (2006.01)

(52) U.S. Cl.
USPC ..... Plt./370

(58) Field of Classification Search
USPC ..... Plt./370
See application file for complete search history.

(56) References Cited

PUBLICATIONS

Printout of application information from Community Plant Variety Office (CPVO) website for corresponding CPVO application No. 2011/2617 filed Nov. 3, 2011 (1 page) (http://www.cpvoextranet.cpvo.europa.eu).

*Primary Examiner* — Annette Para
(74) *Attorney, Agent, or Firm* — Foley & Lardner LLP

(57) ABSTRACT

A new and distinct *Vriesea* plant named 'GLORY' characterized as a funnel form rosette plant, measuring about 30 cm to 35 cm in height (when flowering) and 40 cm to 45 cm in diameter, producing compound, yellow-orange in color (RHS 17A), bipinnate spike inflorescence, measuring about 25 cm in height and about 16 cm in diameter, about 6 to 8 branches, and yellow-green foliage, measuring about 30-35 cm in length and about 3.5 cm to 4.5 cm in width.

2 Drawing Sheets

Latin name of the genus and species of the plant claimed: *Vriesea* sp.

Variety denomination: 'GLORY'.

BACKGROUND OF THE INVENTION

The present invention relates to a new and distinct cultivar of *Vriesea* plant, botanically known as *Vriesea* sp., hereinafter referred to by the cultivar name 'GLORY'. The genus of *Vriesea* belongs to the *Bromeliaceae* family.

The new *Vriesea* cultivar is a product of a planned breeding program conducted by the inventors, Elly Bak and Nico D. M. Steur, in Assendelft, The Netherlands. The objective of the breeding program is to develop a new *Vriesea* variety with good growing habit and attractive inflorescence.

The new *Vriesea* cultivar 'GLORY' originated from a cross-made in a controlled breeding program by the inventors in 1998 in Assendelft, The Netherlands. The female or seed parent is a *Vriesea* selection designated '89326' (unpatented). The male or pollen parent is a *Vriesea* selection designated '93554' (unpatented). 'GLORY' was discovered and selected by the inventors in 2002, as a single flowering plant within the progeny of the stated cross in a controlled environment in Assendelft, The Netherlands.

Asexual reproduction of the new cultivar 'GLORY' performed by vegetative means by tissue culture was first performed in 2007, in Assendelft, The Netherlands. The first 'GLORY' plants propagated through the use of tissue culture flowered in 2009, in Assendelft, The Netherlands, and have demonstrated that the combination of characteristics as herein disclosed for the new cultivar are firmly fixed and retained through successive generations of asexual reproduction. The new cultivar reproduces true-to-type.

BRIEF DESCRIPTION OF THE INVENTION

The following traits have been repeatedly observed and are determined to be unique characteristics of 'GLORY' which in combination distinguish this *Vriesea* as a new and distinct cultivar:

1. Funnel form rosette plant, measuring about 30-35 cm in total height (when flowering) and 40-45 cm in diameter;
2. Compound, yellow-orange (RHS 17A) bipinnate spike inflorescence, measuring about 25 cm in height, and about 16 cm in diameter.
3. About 6 to 8 branches,
4. Yellow green foliage, measuring 30-35 cm in length and 3.5 cm to 4.0 cm in width.

Plants of the parents, '89326' (unpatented) and '93554' (unpatented), are no longer available to provide a botanical comparison with the new *Vriesea* cultivar 'GLORY'. The new cultivar 'GLORY'; differs primarily from plants of the parental cultivars by exhibiting a more branched inflorescence, yellow-orange in color Of the many commercial cultivars known to the present inventors, the most similar in comparison to the new *Vriesea* cultivar 'GLORY' is the *Vriesea* cultivar designated 'STYLE' (U.S. Plant Pat. No. 18,176). Plants of the new cultivar 'GLORY' differ from plants of 'STYLE' primarily in inflorescence color.

The new *Vriesea* cultivar 'GLORY' can also be compared to the *Vriesea* cultivar designated 'ENERGY' (U.S. Plant Pat.

No. 18,235). Plants of the new cultivar 'GLORY' differ from plants of 'ENERGY' primarily in number of branches ('ENERGY' has fewer branches).

BRIEF DESCRIPTION OF THE PHOTOGRAPHS

The accompanying photograph illustrates the overall appearance of the new *Vriesea* cultivar 'GLORY' showing the colors as true as is reasonably possible with colored reproductions of this type. Colors in the photograph may differ slightly from the color values cited in the detailed botanical description which accurately describes the color of 'GLORY'.

DETAILED BOTANICAL DESCRIPTION

Figure 1:
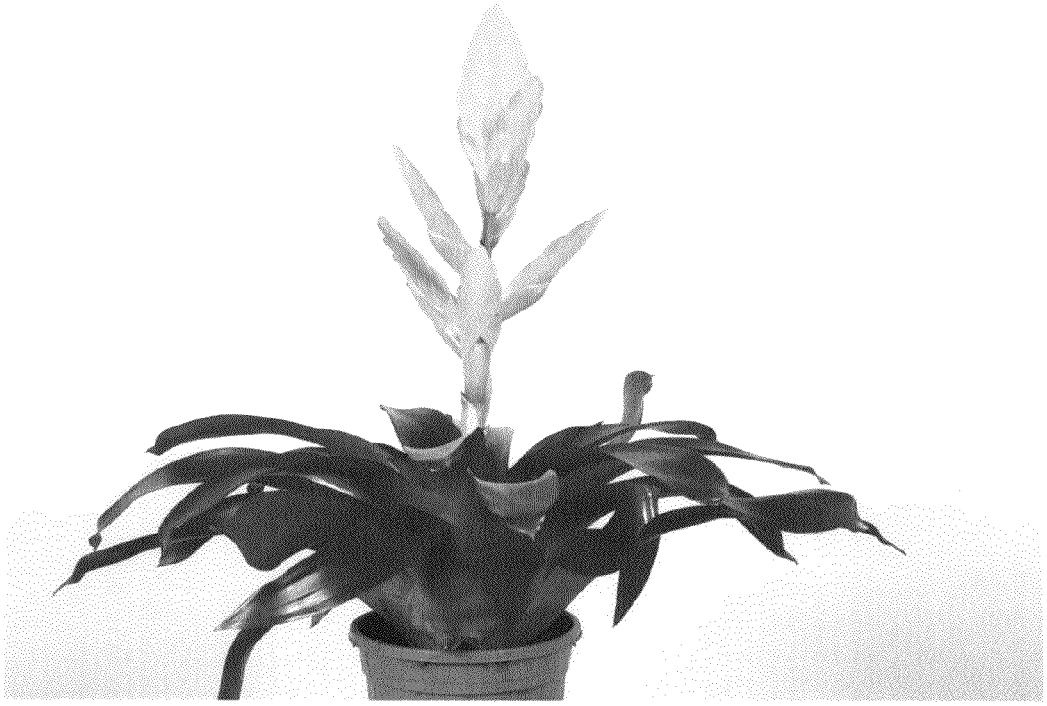
FIG. 1 shows a side perspective view of a typical potted flowering plant of 'GLORY' at about 18 months of age from potting.
Figure 2:
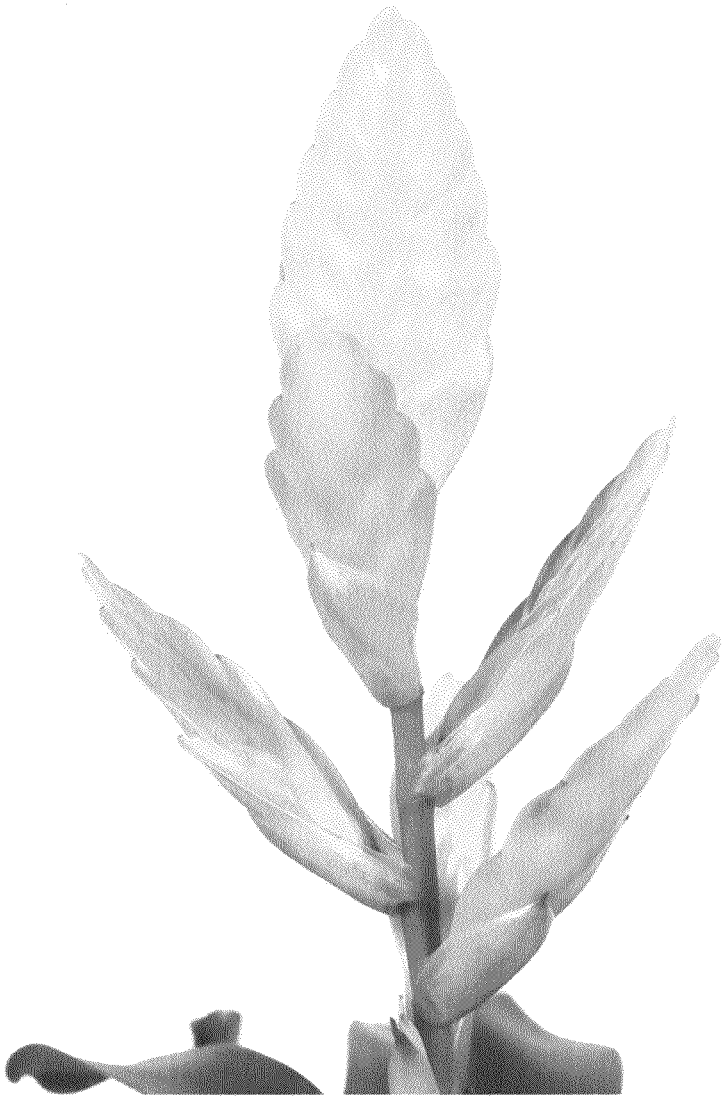
FIG. 2 shows a close-up view of a bract of 'GLORY' at about 18 months of age from potting.

'GLORY' has not been observed under all possible environmental conditions. The phenotype of the new cultivar may vary with variations in environment such as temperature, light intensity, day length, fertilizers and humidity without any change in the genotype of the plant.

The afore mentioned photographs, together with the following observations, measurements and values describe the new *Vriesea* cultivar as grown in a greenhouse in Assendelft, The Netherlands, under conditions which closely approximate those generally used in commercial practice. Plants of 'GLORY' were grown in a greenhouse with day temperatures ranging from 20° C. to 28° C. and night temperatures ranging from 18° C. to 23° C. No artificial lighting or photoperiodic treatments were conducted, but plants of 'GLORY' are forced into flowering. The following fertilizer is added when growing plants of 'GLORY': 1 part nitrogen, 0.6 parts phosphor, 2 parts Kalium and 0.1 parts magnesium.

Color references are made to The Royal Horticultural Society Colour Chart (R.H.S.), except where general colors of ordinary significance are used. Color values were taken under daylight conditions in a greenhouse in Assendelft, The Netherlands. The age of the plants of 'GLORY' described is about 15 months from potting.

Classification:

*Botanical.*—*Vriesea* sp.

Parentage:

*Male parent.*—*Vriesea* sp. cultivar designated '93554' (unpatented).

*Female parent.*—*Vriesea* sp. cultivar designated '89326' (unpatented).

Propagation: Tissue culture.

Plant:

*General appearance and form.*—Height: About 30-35 cm (when flowering). Width: About 40-45 cm. Shape: Funnel form rosette. Growth habit: Stemless. Plant Vigor: Good. Flowering Season: A fully grown plant can flower year round, starting 15 to 17 weeks after induction of natural light or trough flowering treatment. Cold Tolerance: Frost tender. Temperatures below 5° C. may damage plants. Fragrance: None.

Foliage:

*Quantity.*—About 25 to 35.

*Size of mature leaf.*—Length: About 30-35 cm. Width: About 3.5-4 cm.

*Overall shape.*—Broad and linear.

*Apex shape.*—Abruptly acuminate.

*Base shape.*—Strap-like around central axis.

*Margin.*—Entire.

*Texture.*—Smooth and glabrous.

*Color.*—Leaf color can vary depending on growing conditions. Upper Surface: Mature leaf: Yellow-green, RHS 147A. Immature leaf: Yellow-green, RHS 147A. Lower Surface: Mature leaf: Yellow-green, RHS 147B. Immature leaf: Yellow-green, RHS 147B.

Inflorescence:

*Quantity and form.*—1 flower per floral bract, typical for the genus *Vriesea*; flowering is normally in progression from base to tip of scape.

*Shape.*—Bipinnate spike (main spike about 11 cm in length and about 5 cm in width, side spike about 10 cm in length and about 3.5 cm in width).

*Size.*—Height: about 25 cm. Diameter: about 16 cm.

*Color.*—Yellow-Orange, RHS 17A.

*Corolla.*—Form: Long and narrow, petals and sepals fused at the base around the ovary. Number: About 75 depending on the size of the plant.

*Petals.*—Number: 3 per flower. Length: About 4 cm. Width: About 0.6 cm. Overall Shape: Ligulate. Apex Shape: Obtuse. Base Shape: Fused. Color: Upper surface: Yellow, RHS 5A. Lower surface: Yellow, RHS 5A.

*Sepals.*—Number: 3 per flower. Length: About 2.5 cm. Width: About 0.9 cm. Overall Shape: Ligulate. Apex Shape: Acute. Base Shape: Fused. Color: Translucent, Yellow, closest to RHS 12B.

*Branches.*—Quantity: About 6-8. Length: About 10-11 cm. Width: About 3.5-5 cm. Color: Yellow-Orange, RHS 17A.

*Scape.*—Color: Red, RHS 46A.

*Bracts.*—Quantity of bracts on main spike: About 17. Arrangement: Alternate. Size: Length: About 3.5-4.5 cm. Width: About 2.5-3 cm. Overall shape: Ovate. Color: Yellow-Orange, RHS 17A.

Reproductive organs:

*Androecium.*—Stamen: Number: 6 per flower. Length: About 3.5 cm. Diameter: About 0.1 cm. Color: Yellow, RHS 11C. Anther: Length: About 0.6 cm. Color: Yellow, RHS 11C. Pollen: Amount: Scarce. Color: Yellow, too small to qualify RHS.

*Gynoecium.*—Pistil: Number: 1 per flower. Length: About 4.5 cm. Stigma: Shape: 3-parted. Width: About 0.4 cm. Color: Yellow-green, RHS 144C. Style: Length: About 4.5 cm. Color: Yellow, RHS 11C. Ovary: Shape: Conical. Length: About 0.8 cm. Diameter: About 0.3 cm. Color: Yellow, RHS 11C.

Disease/pest resistance: No information is currently available.

Disease/pest susceptibility: No information is currently available.

We claim:

1. A new and distinct *Vriesea* plant named 'GLORY', substantially as illustrated and described herein.

* * * * *